United States Patent
Harvey et al.

(10) Patent No.: US 7,198,172 B2
(45) Date of Patent: Apr. 3, 2007

(54) MEDICAMENT DISPENSER

(75) Inventors: Stephen James Harvey, Ware (GB); Daniel Thomas de Sausmarez Lintell, Ware (GB)

(73) Assignee: Glaxo Group Limited, Greenford (GB)

( * ) Notice: Subject to any disclaimer, the term of this patent is extended or adjusted under 35 U.S.C. 154(b) by 60 days.

(21) Appl. No.: 10/513,101

(22) PCT Filed: Apr. 25, 2003

(86) PCT No.: PCT/EP03/04407

§ 371 (c)(1),
(2), (4) Date: Oct. 29, 2004

(87) PCT Pub. No.: WO03/092773

PCT Pub. Date: Nov. 13, 2003

(65) Prior Publication Data

US 2005/0177275 A1 Aug. 11, 2005

(30) Foreign Application Priority Data

Apr. 29, 2002 (GB) ................. 0209783.0

(51) Int. Cl.
*G07F 11/00* (2006.01)
(52) U.S. Cl. ........................................ 221/8
(58) Field of Classification Search .............. 221/71, 221/17, 8, 6, 4, 2; 128/200.23; 206/459.1, 206/459.5; 434/262
See application file for complete search history.

(56) References Cited

U.S. PATENT DOCUMENTS

| 4,223,801 A | 9/1980 | Carlson |
| 4,419,016 A | 12/1983 | Zoltan |
| 4,588,303 A | 5/1986 | Wirtschafter et al. |
| 5,363,842 A | 11/1994 | Lanpher et al. |
| 5,408,443 A | 4/1995 | Weinberger |
| 5,412,372 A | 5/1995 | Parkhurst et al. |
| 5,505,195 A | 4/1996 | Sallis et al. |
| 5,583,832 A | 12/1996 | DePonty |
| 5,809,997 A | 9/1998 | Wolf |
| 6,012,450 A | 1/2000 | Rubsamen |
| 6,014,969 A | 1/2000 | Lloyd et al. |
| 6,102,855 A | 8/2000 | Farrage et al. |
| 6,252,494 B1 | 6/2001 | Howell |

FOREIGN PATENT DOCUMENTS

| EP | 0857456 | 8/1998 |
| EP | 0933092 | 8/1999 |
| EP | 1161933 | 12/2001 |
| WO | WO 99/38556 | 8/1999 |
| WO | WO 99/43284 | 9/1999 |
| WO | WO 00/21598 | 4/2000 |
| WO | WO 01/41845 | 6/2001 |
| WO | WO 01/50434 | 7/2001 |
| WO | WO 01/93801 | 12/2001 |
| WO | WO 02/078593 | 10/2002 |

*Primary Examiner*—Gene O. Crawford
*Assistant Examiner*—Timothy Waggoner
(74) *Attorney, Agent, or Firm*—James P. Riek

(57) ABSTRACT

Disclosed is a medicament dispenser having a base unit and a replaceable refill container. The base unit has one or more sensors for sensing one or more conditions of the medicament dispenser and a display for displaying indicia representing a state of the medicament dispenser. First indicia show the base unit and second indicia show the refill container. The display of at least one of said first and said second indicia is selectively controllable independently of the display of the other of said first and said second indicia in order to indicate said one or more sensed conditions of the medicament dispenser.

36 Claims, 11 Drawing Sheets

MEDICAMENT DISPENSER

CROSS-REFERENCE TO RELATED APPLICATIONS

This application is filed pursuant to 35 USC 371 as a United States National Phase Application of International Patent Application Serial No. PCT/EP03/04407 filed on 25 Apr. 2003, which claims priority from GB 0209783.0 filed on 29 Apr. 2002 in the United Kingdom.

TECHNICAL FIELD

The present invention relates to a medicament dispenser for dispensing medicament. The invention particularly, but not exclusively, relates to an inhalation device for use in dispensing medicament.

BACKGROUND TO THE INVENTION

The use of inhalation devices in the administration of medicaments, for example in bronchodilation therapy is well known. Such devices generally comprise a body or housing within which a medicament container is located. Known inhalation devices include those in which the medicament container is a blister strip containing a number of discrete doses of powdered medicament. Such devices usually contain a mechanism for accessing these doses, usually comprising either piercing means or means to peel the lid sheet away from the base sheet. The powdered medicament can then be accessed and inhaled.

It would be desirable to provide a portable medicament dispenser (e.g. an inhalation device) which is refillable by insertion of a replacement container containing a medicament. The container may then be replaced when the medicament content is empty, allowing the majority of the dispenser to be retained. This allows the retained part of the dispenser to be fitted with additional features such as an electronics subsystem which may not be cost effective on a completely disposable and portable dispenser.

It is a further object of the present invention that the refill container may be easily removed and that a new refill container can be easily inserted. It is also desirable that the operation of the medicament dispenser is clear and non-complex to a user and that any steps involved in preparing the dispenser for use are minimised and simplified.

SUMMARY OF THE INVENTION

According to one aspect of the present invention, there is provided a medicament dispenser comprising a base unit, the base unit being adapted for receiving a replaceable refill container and for sensing one or more conditions of the medicament dispenser, said base unit comprising display means for displaying indicia representing a state of the medicament dispenser, wherein said display means are configured to display:

first indicia providing a graphical representation of the base unit; and second indicia providing a graphical representation of a refill container, wherein the display of at least one of said first and said second indicia is selectively controllable independently of the display of the other of said first and said second indicia in order to indicate said one or more sensed conditions of the medicament dispenser.

According to a further aspect of the invention, there is provided a medicament dispenser comprising a base unit, the base unit being adapted for receiving a replaceable refill container, said base unit comprising a display for displaying indicia representing a state of the medicament dispenser, wherein said display means are configured to display:

first indicia providing a graphical representation of a physical appearance of at least part of the medicament dispenser; and second indicia representing one or more sensed conditions of the medicament dispenser, wherein said medicament dispenser includes a mechanical priming component for initiating the dispensing of medicament and said second indicia comprise indicia representing actuation of the mechanical priming component.

The present invention provides a medicament dispenser capable of providing clear and concise status indications to the user during operation of the device in response to sensed operating conditions.

Furthermore, the indications may be provided without the need for textual output, thereby simplifying the display structure and making the device suitable for use by users having varying different mother tongues and of varying ages.

Features and advantages of the present invention will become apparent from the following description of preferred embodiments of the invention, given by way of example only, made with reference to the accompanying drawings.

DETAILED DESCRIPTION OF THE DRAWINGS

Figure 1:
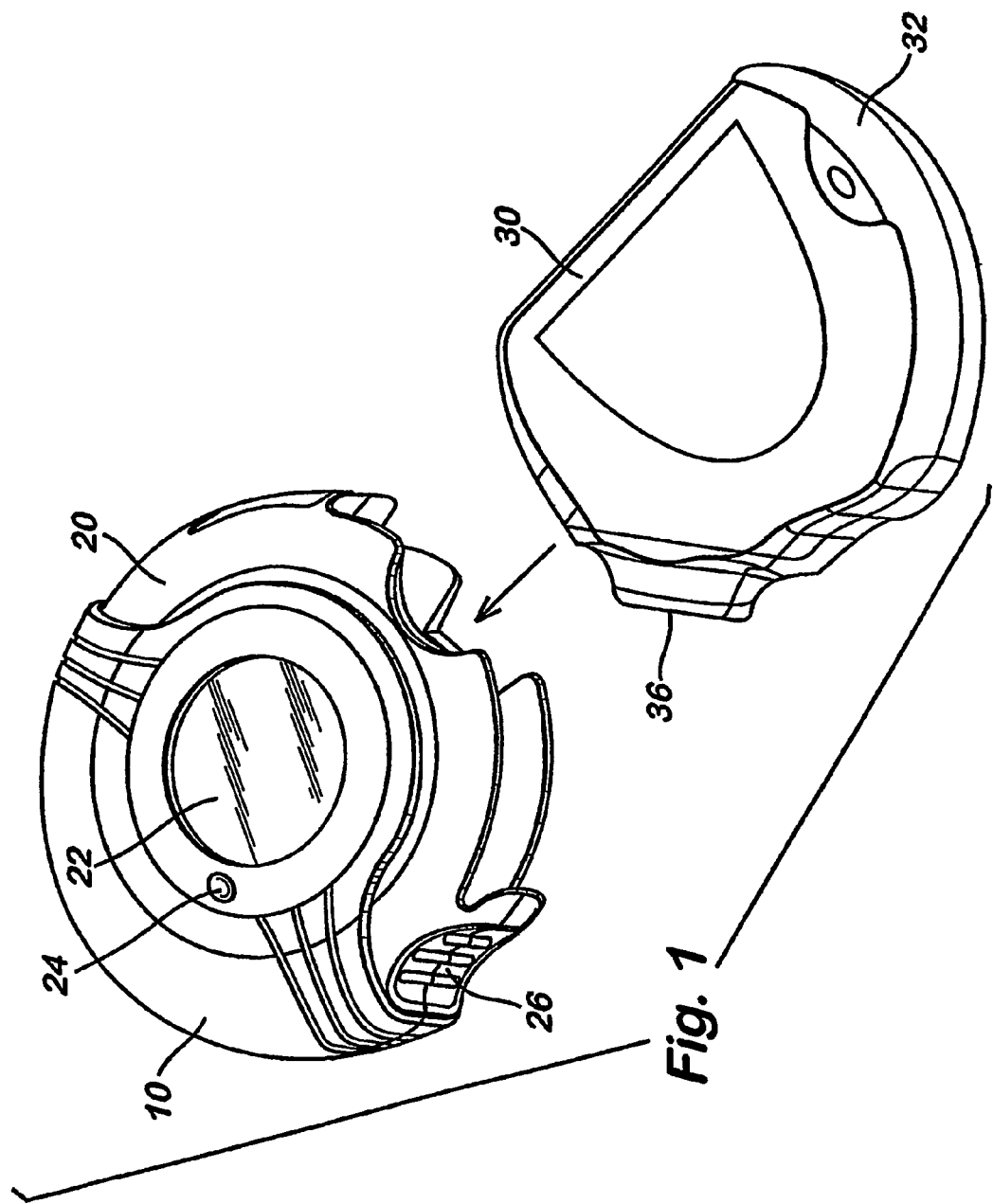
FIG. 1 shows a perspective view of a medicament dispenser according to an embodiment of the invention with the cassette removed from the holder and body.

FIG. 1 shows a medicament dispenser in accordance with an embodiment of the present invention, in the form of a base unit comprising an outer cover 10 and a holder 20, and a refill cassette 30. The holder 20 includes an electronic display 22 and an associated button 24. The holder 20 is shaped to fit inside cover 10 and is fixed to the body via a bearing (not shown) about which it rotates coaxially. Stops (not shown) protrude from the holder 20 and prevent the holder 20 from rotating more than about 180° relative to the cover 10. The stops also provide two defined positions of the holder 20 within the cover 10. One position is defined by a stop meeting with a part of the cover 10 and the other position defined by the other stop meeting with another part of the cover 10 when the holder has been rotated relative to the body. An outer part of the holder is shaped in the form of a concave recess 26 to provide a thumb or finger grip for the user of the device. The holder 20 forms a recess into which the refill cassette 30 latches.

The refill cassette 30 comprises a shell containing the medicament carrier and a mechanism for opening the carrier for the medicament to be accessed (see FIG. 7). The refill cassette 30 has a rear end 32 which is exposed by a cut-away portion of the holder 20 when the rest of the cassette 30 is contained within the holder 20 so as to allow the cassette to be manually gripped for removal from the holder 20.

The refill cassette 30 also has a mouthpiece 36 from which a user inhales medicament dispensed from the cassette 30.

Figure 2:
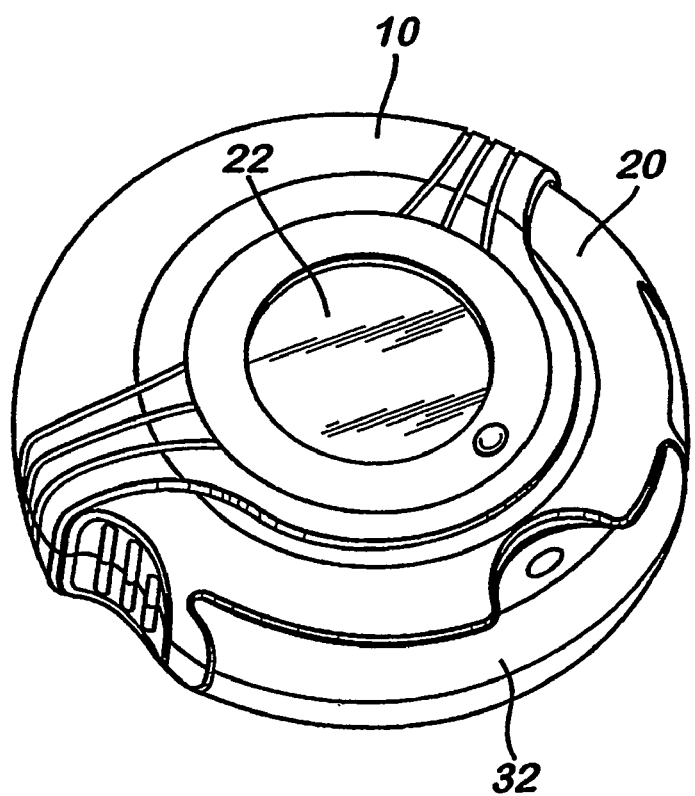
FIG. 2 shows a perspective view of the medicament dispenser of FIG. 1 with the cassette inserted into the holder and body in the non-dispensing position.

FIG. 2 shows the medicament dispenser with the cassette 30 in place in the holder 20 and with cover 10 in a non-dispensing position in which the rear end 32 of the cassette is exposed. The cassette 30 is fixed in place by a spring-biased catch (not shown). When the cassette 30 is in the position shown, relative to the holder 20, the cover 10 covers the mouthpiece (not shown). The cover 10 also protects the thumbtab of an indexing lever (not shown) and this prevents accidental indexing of the medicament carrier when the medicament dispenser is not in use.

Figure 3A:
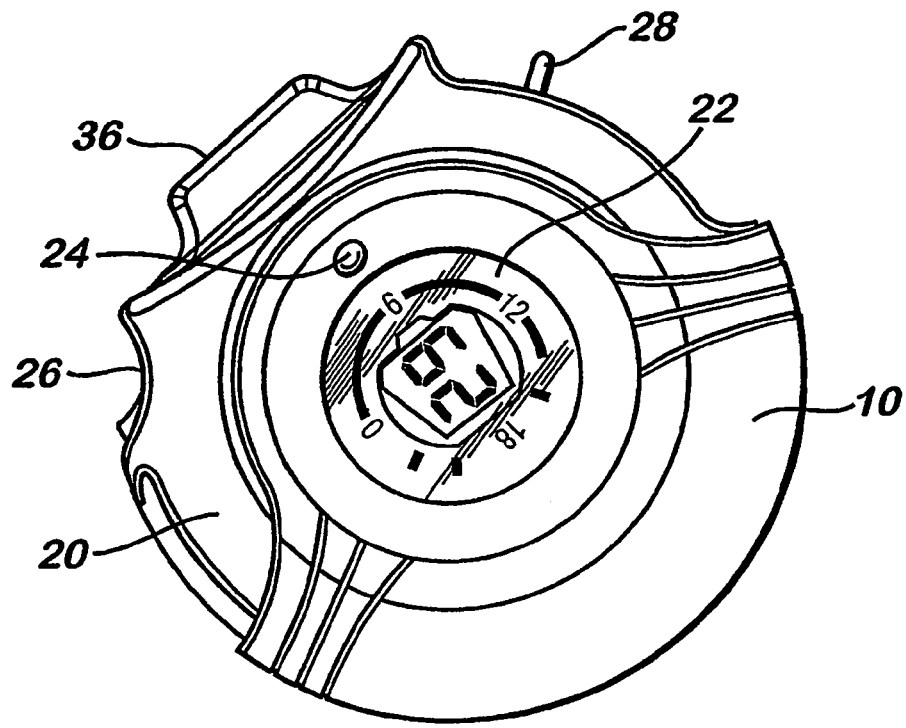
FIGS. 3a and 3b show plan views of the medicament dispenser of FIGS. 1 and 2 with the cassette in the dispensing position.
Figure 3B:
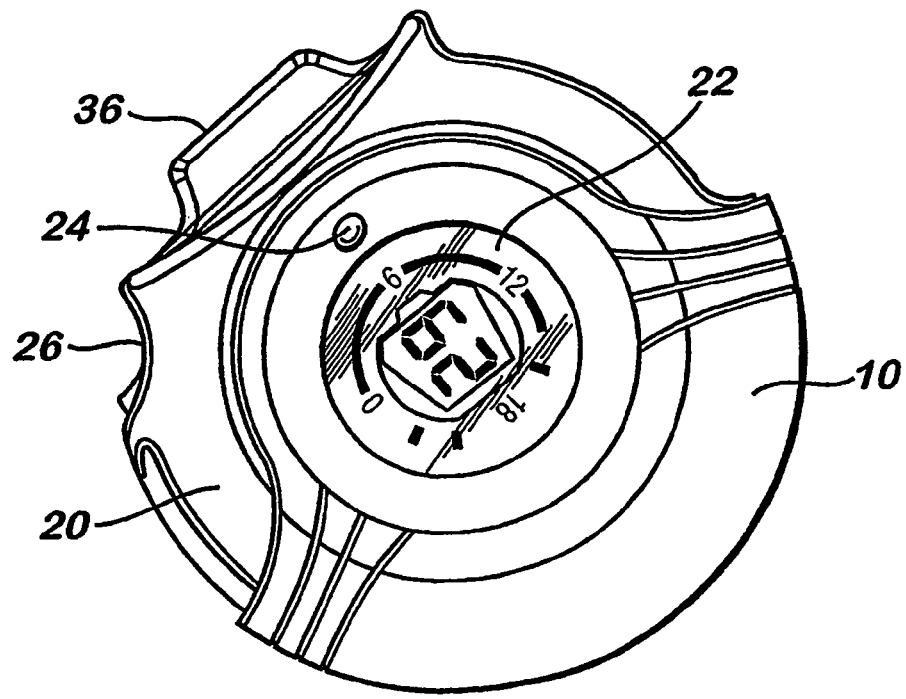

FIGS. 3a and 3b show the medicament dispenser of FIGS. 1 and 2 with the cassette 30 in place in the holder 20 in a dispensing position. The holder 20 has been rotated relative to the cover 10 so that a stop on the holder 20 abuts the cover 10. It can be seen that the holder 20 has a further cut away portion to expose the mouthpiece 36.

FIG. 3a shows the thumbtab 28 of the indexing lever in a reset position, ready for actuation. Actuation of the thumbtab 28 indexes the medicament carrier within the refill cassette 30, thereby exposing a dose of medicament ready for inhalation through the mouthpiece 36. FIG. 3b shows the configuration of the dispenser after the thumbtab 28 has been actuated. The thumbtab sits within the recess covered by the dispenser cover 10. Rotation of the holder 20 within the cover 10 following actuation of the thumbtab 28 resets the thumbtab 28 to its reset position shown in FIG. 3a The display 22 shown in FIGS. 3a and 3b includes a graphical representation of the medicament dispenser, including a base unit icon, a refill icon, a set of time elapsed indicia and a set of dose count indicia, to be described in further detail below. Note that the indicia representing the medicament dispenser provide a graphical representation of the external appearance of the refill cassette and holder together when attached. The representation is aligned with the actual holder, such that the orientation of the mouthpiece of the graphical representation coincides with that of the mouthpiece 36, thereby increasing understandability of the display.

Figure 4:
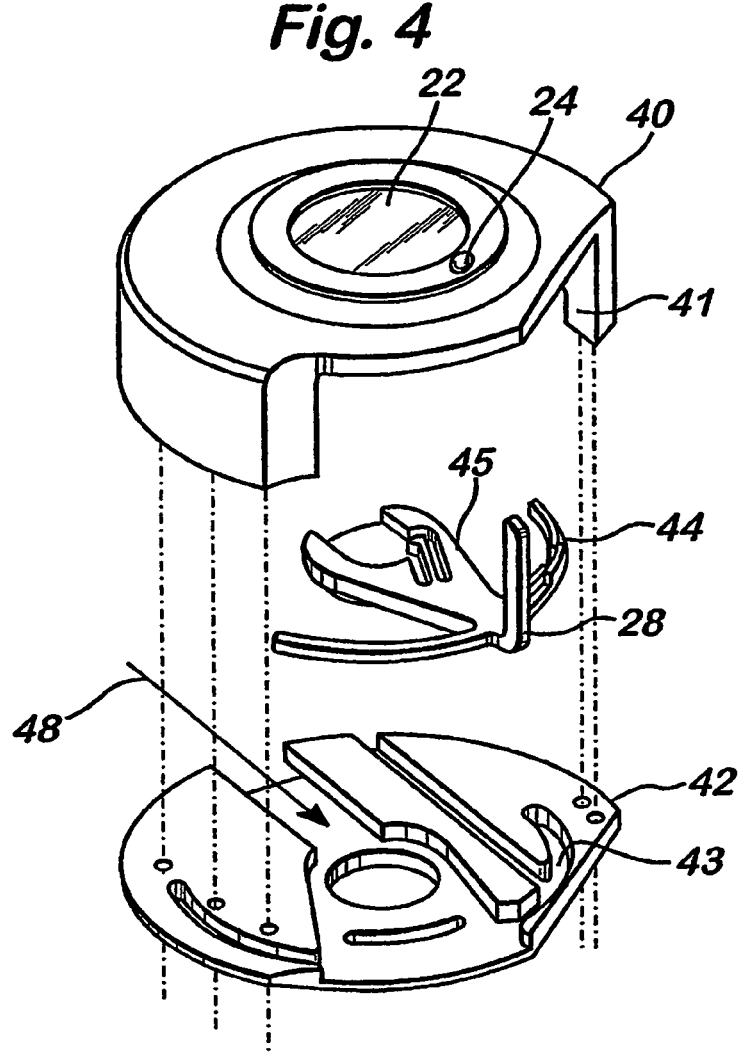
FIG. 4 is an exploded perspective view of a holder.

FIG. 4 is a vertically exploded perspective view of elements of the holder 20. The holder 20 includes an upper shell 40, on which the display 22 and the button 24 are rigidly mounted, and a base 42. The base 42 includes an arcuate channel 40 in which a corresponding arcuate element 44 is mounted to provide coaxial movement of the thumbtab 28 of indexing lever 45, whereby priming of the refill cassette 30 is achieved. When inserting a new refill cassette 30 in the holder 20, a ratcheted gear 46, attached to its spindle inside the refill cassette 30, moves along a linear groove, as represented by arrow 48, in the holder 20, towards a central axial location within which the lever 45 acts on gear 46 to rotate the spindle in response to movement of the thumbtab 28. It can also be seen that the upper shell 40 includes a cut-out portion 41 whereby mouthpiece 36 is exposed in the holder after insertion thereof.

Figure 6:
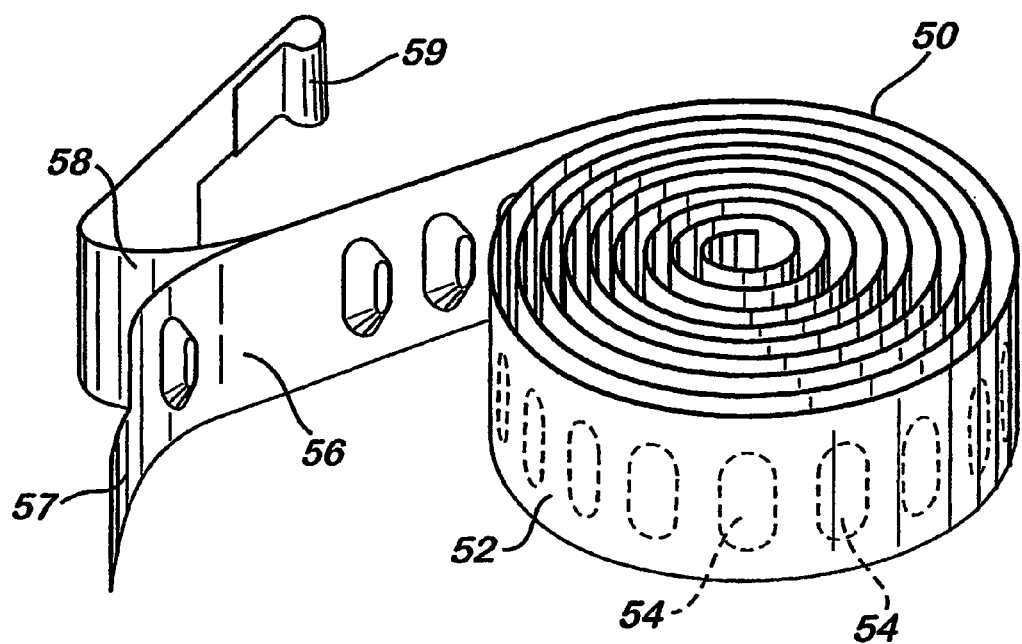
FIG. 6 shows a perspective view of a medicament carrier for use in accord with the present invention.

FIG. 6 shows a medicament carrier 50 for use in an embodiment of the invention. The medicament carrier comprises a peelable blister strip 52 defining a plurality of pockets 54 each of which contains a dose of medicament which can be inhaled, in the form of powder.

The strip comprises a base sheet 56 in which blisters are formed to define the pockets 54 and a lid sheet 58 which is hermetically sealed to the base sheet except in the region of the blisters in such a manner that the lid sheet 58 and the base sheet 56 can be peeled apart. The sheets 56, 58 are sealed to one another over their whole width except for the leading end portions 57, 59.

The lid 58 and base 56 sheets are each preferably formed of a plastics/aluminium laminate and are preferably adhered to one another by heat sealing.

The strip 52 is shown as having elongate pockets 54 which run transversely with respect to the length of the strip 52. This is convenient in that it enables a large number of pockets 54 to be provided in a given strip length. The strip 52 may, for example, be provided with from fifty to one hundred pockets 54 but it will be understood that the strip 52 may have any suitable number of pockets 54.

Figure 7A:
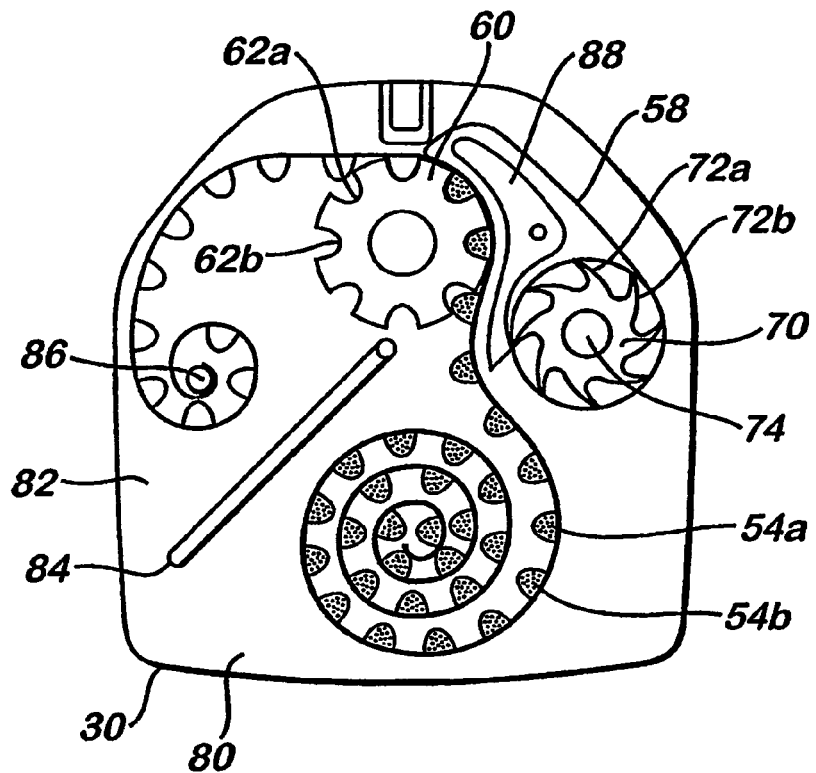
FIGS. 7a and 7b show a schematic view of an internal mechanism of a cassette in accordance with an embodiment of the present invention.
Figure 7B:
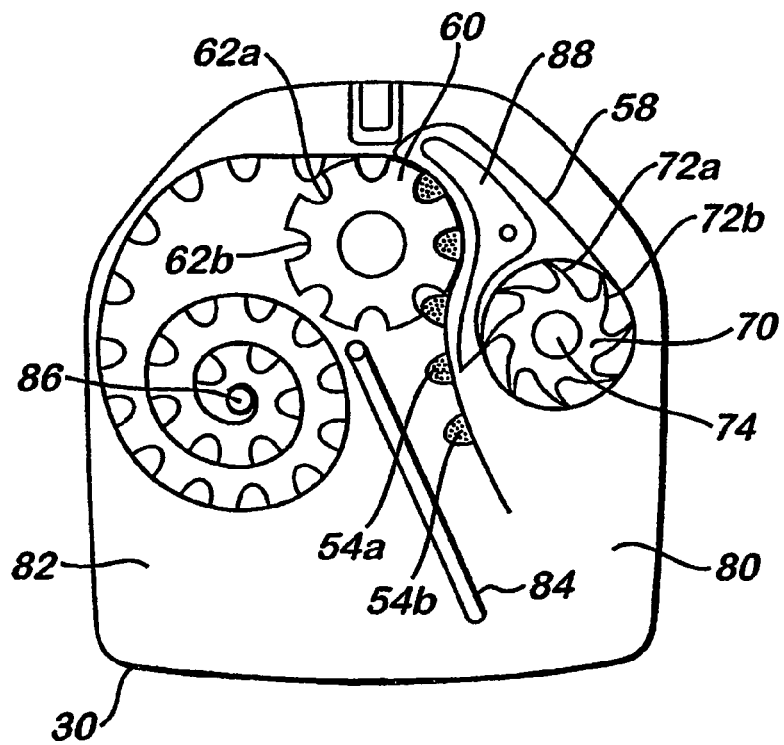

FIGS. 7a and 7b schematically show an internal mechanism of a refill cassette 30 containing a medicament carrier in one embodiment of the invention. FIG. 7a shows the medicament carrier in the situation where the majority of the pockets are still filled with discrete doses of medicament in the form of dry powder. FIG. 7b shows the situation where the majority of pockets are empty and most of the lid sheet 58 has been removed from the base sheet 56.

The internal mechanism comprises an index wheel 60 and a lid-winding wheel 70 for winding the used portion of the lid sheet 58. The index wheel 60 has a plurality of recesses 62a, 62b extending parallel with the axis of the wheel. The recesses 62a, 62b are spaced at a pitch which is equal to the distance between the centre lines of adjacent pockets 54a, 54b.

Figure 5:
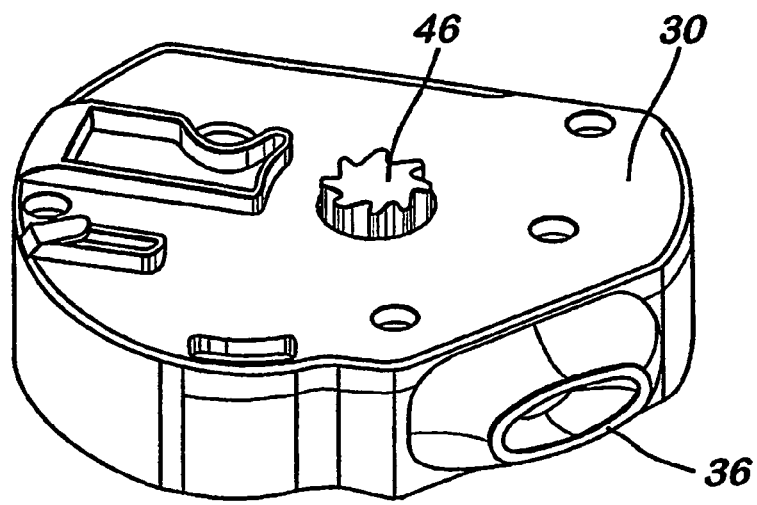
FIG. 5 is a perspective view of a refill cassette from below.

The cassette 30 also includes an area 80 for the medicament carrier to be coiled in prior to use of the doses contained inside it and an area 82 where the used base of the medicament carrier is collected. Area 82 contains base winding wheel 86 on which the used portion of the base sheet is wound. Also included is a movable wall 84 to separate these two areas to separate the two areas 80, 82. The movable wall 84 is pushed from the position shown in FIG. 5a by the growing coil of collected base sheet to the position shown in FIG. 5b, thereby adjusting the size of the areas respectively.

The spindle mechanism (not shown) is arranged to unidirectionally rotate the index wheel 60 and the lid-winding wheel 70 in unison and base winding wheel 86.

The lid winding wheel shown in FIGS. 7a and 7b takes the form of a collapsible wheel 70. The collapsible wheel 70 has a series of resilient arms 72a, 72b radiating from a central shaft 74, each at an angle to a radius. The leading end of the lid sheet 58 is looped over one of these resilient arms 72a and the lid sheet 58 is wound onto the collapsible wheel 70 as it is peeled away from the base sheet 56. As more lid sheet 58 is wound onto the collapsible wheel 70, the resilient arms 70a, 70b gradually flex inwardly, and the effect is to keep the external diameter of the reel of wound up lid sheet 58 substantially constant while the internal diameter decreases.

Guide portion 88 guides the lid sheet from the point at which it is separated from the base sheet to the lid winding wheel.

In operation, the user moves the holder relative to the body to move the cassette into the dispensing position and then presses on the finger tab of the lever to cause it to move. This leads to rotation of the index wheel which results in rotation of both the base winding wheel and the lid winding wheel, thus peeling the base sheet and lid sheet apart over a distance sufficient to expose a previously unopened pocket opposite the end of the powder outlet. The patient can then inhale the powdered medicament through the mouthpiece.

Figure 8:
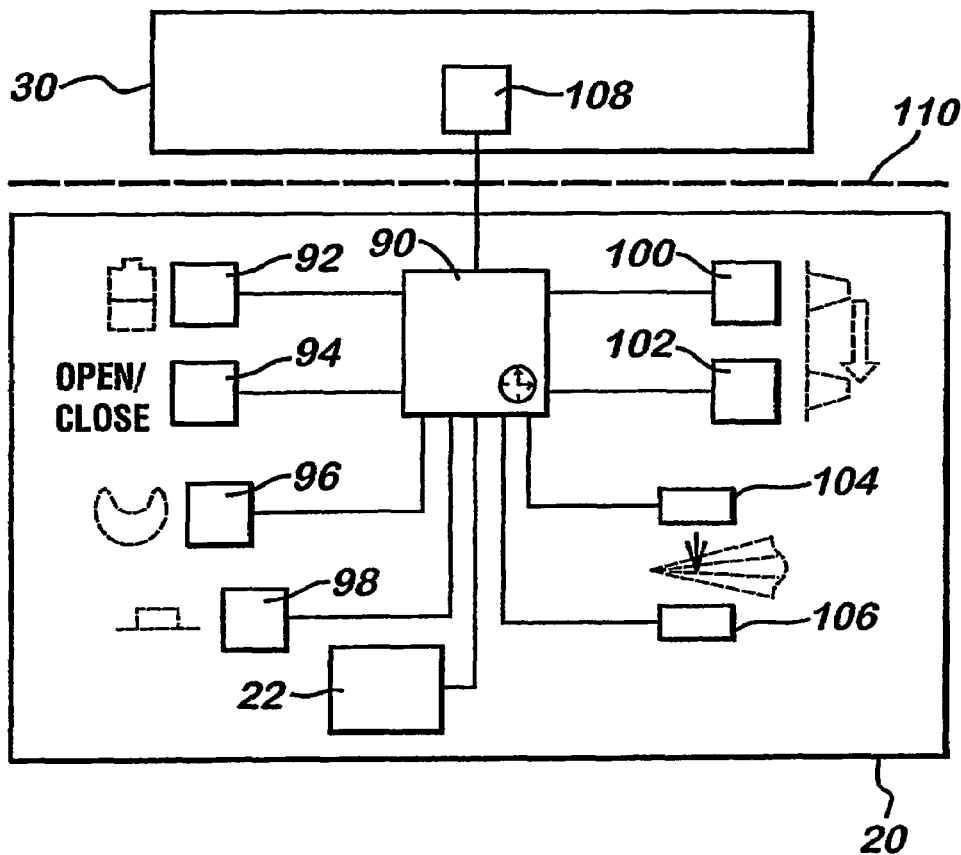
FIG. 8 is a schematic block diagram of an electronic subsystem of the medicament dispenser.

FIG. 8 is a schematic block diagram of the electronic subsystem of the medicament dispenser. The holder 20 includes an in-built control unit 90, for example in the form of a microprocessor chip, including an internal clock. Various sensors are electrically connected to the control unit 90, including a battery power level sensor 92, which senses the remaining power level of a battery providing electrical power to the medicament dispenser, also housed in the holder 20. A cover open sensor 94 senses movement of the cover relative to the holder from the non-dispensing position, in which the cover covers the mouthpiece of the dispenser, to an open position in which medicament may be dispensed. A refill attach sensor 96 is associated with the mechanical connection mechanism whereby a refill cassette is attached to a holder. When a refill is correctly attached, refill attach sensor 96 detects the correct attachment. When a refill is not attached, this can also be sensed using refill attach sensor 96. A button switch 98 senses actuation of the button 24. A priming reset sensor 100 senses the position of the index lever in its reset position, whereas a priming actuation sensor 102 senses the position of the index lever in its fully actuated position. Together sensors 100 and 102 are used to detect movement of the index lever from its reset position to the actuated position to indicate the presentation of a new dose of medicament within the refill, which the user may take by inhaling through the mouthpiece. A radiation emitter 104 emits radiation into the mouthpiece, whilst an inhalation sensor 106 detects the emitted radiation on the other side of the mouthpiece. Together, the radiation emitter 104 and 106 are used to indicate the inhalation of a dose by the user. When the user inhales, the medicament powder causing scattering of the radiation emitted by radiation emitter 104, thereby reducing the detected level of radiation at inhalation sensor 106, indicating the inhalation of a dose.

The refill cassette 30 includes a memory chip 108, which is in data communication with the control unit 90 via a data communication interface 110. The data communication interface uses a transceiver in the control unit 90 and a transceiver in the memory chip 108, which communicate via electrical connections made when the refill cassette 30 is inserted within the holder 20. Alternatively, the memory chip 108 may be in the form of a radio frequency (RFID) tag, and the data communications interface 110 may be a wireless data communications interface. Finally, the control unit 90 is operatively connected to the display 22, for controlling the display in accordance with sensed conditions of the medicament dispenser.

Various different conditions of the medicament dispenser may be sensed by means of the electronic subsystem illustrated in FIG. 8. These are as follows:

1. A refill attached condition, sensed by refill attached sensor 96.
2. A refill not attached condition, sensed by refill attached sensor 96.
3. A refill authenticated condition. When a refill cassette 30 is attached to the holder 20, the control unit 90 reads data from the memory chip 108. The data includes a current dose count for the refill cassette, and authentication data, such as a unique ID and an associated digital signature. The control unit 90 stores an authentication algorithm, whereby the data read from the memory chip 108 may be authenticated. If authenticated, the refill authenticator condition is hence sensed.
4. A refill invalid condition. If the authentication process carried out by the control unit when the refill is attached fails to authenticate the refill cassette 30, the refill invalid condition is generated.
5. A dose count condition. The dose count read from the memory chip 108. When a dose is dispensed from the refill cassette 30, the control unit 90 updates the current dose count on the memory chip 108 by decrementing the current dose count. Thus, the dose count condition indicates a sensed number of doses in the refill cassette 30.
6. A low dose remaining condition. When the number of doses within the refill cassette 30 falls below a preset threshold, the low dose remaining condition is generated.
7. A no dose remaining condition, at which point the refill cassette 30 should be removed and a new refill cassette should be inserted.
8. A dose not due condition. After a dose is dispensed and/or inhaled, the control unit 90 begins a time elapsed function, which monitors a time elapsed since a dose was sensed to have been taken. The control unit 90 uses a timing regimen, which may be preset in the control unit 90 or read from the memory chip 108, to determine the length of time between dose reminders. For example, the timing regimen may operate on a 12 hour interval, in which case a dose is ideally taken at 12 hour intervals. If the current time elapsed since the last taking of the dose is within the interval, the medicament dispenser is sensed to be within a dose not due condition.
9. A dose due condition. If the current time elapsed since the taking of the last dose is greater than the dose reminder interval, a dose due condition is generated by the control unit 90.
10. A dose primed condition. Using priming reset and actuation sensors 100, 102, the control unit 90 senses when a dose has been primed within the refill cassette 30, to generate the dose primed condition.
11. A dose inhaled condition. The control unit 90 uses radiation emitter 104 and inhalation sensor 106 to detect inhalation of a primed dose. On inhalation, the dose inhaled condition is generated.
12. A low battery level condition, as sensed by battery power level sensor 92.

Each of FIGS. 9, 18, 19, 20, 21 and 22 show alternative embodiments 22*a–f* of screen layout for the display 22, whereby the various sensed conditions may be indicated to the user. Note that although not illustrated in FIG. 8, the electronic subsystem may also include other forms of indicators, such as an audible alarm generator, which may be used, alone or in combination with visual display on the display, to indicate the generation of a new sensed condition in the medicament dispenser. For example, when a dose due condition is generated, the medicament dispenser may indicate the sensed condition on the display, and also provide an audible alarm at intervals which increase in frequency and/or volume whilst the dose due condition remains. Each of the display configurations 22*a*, 22*b*, 22*c*, 22*d*, 22*e*, 22*f* are generated on a segmented LCD display. In a segmented LCD display, the display indicia are formed by means of individual liquid crystal elements which are preconfigured in the display screen, and which may be separately activated under the control of the control unit 90. An advantage of using a segmented display is increased clarity, along with reduced cost. However, other forms of display means may also be used, such as a pixellated LCD display, whereby indicia are formed using combined actuation of sets of pixels within the display. The display may be monochrome or colour. Again, for increased clarity and reduced cost, a monochrome display is preferred. Some indicia on the display may be static indicia. For example, where the display shows a graphical representation of a base unit, then there is no need to hide the base unit in order to provide indication of any of the sensed conditions, the indicia forming the graphical representation of the base unit may be placed on the display in static form, for example by being preprinted onto the screen surface.

Note that each of FIGS. 9, 18, 19, 20, 21 and 22 are shown with all indicia activated. In operation, the control unit will selectively display indicia in accordance with the current state of the medicament dispenser, in order to indicate one or more current sensed conditions of the medicament dispenser at any one time. Thus, some indicia will be activated whilst others are hidden.

Note that, below, the description of elements of each of the screen configurations 22*a*–*f* are to be understood to apply to the same icons and indicia displayed in each of the different screen configurations where the same numerical references, incremented by multiples of 100, are used. Although the exact form of the icons and indicia are different, their functions and the control thereof by the control unit 90 are similar and therefore should be understood that the description in relation to icons and indicia in one configuration applies equally to similarly referenced icons and indicia in different configurations.

Figure 9:
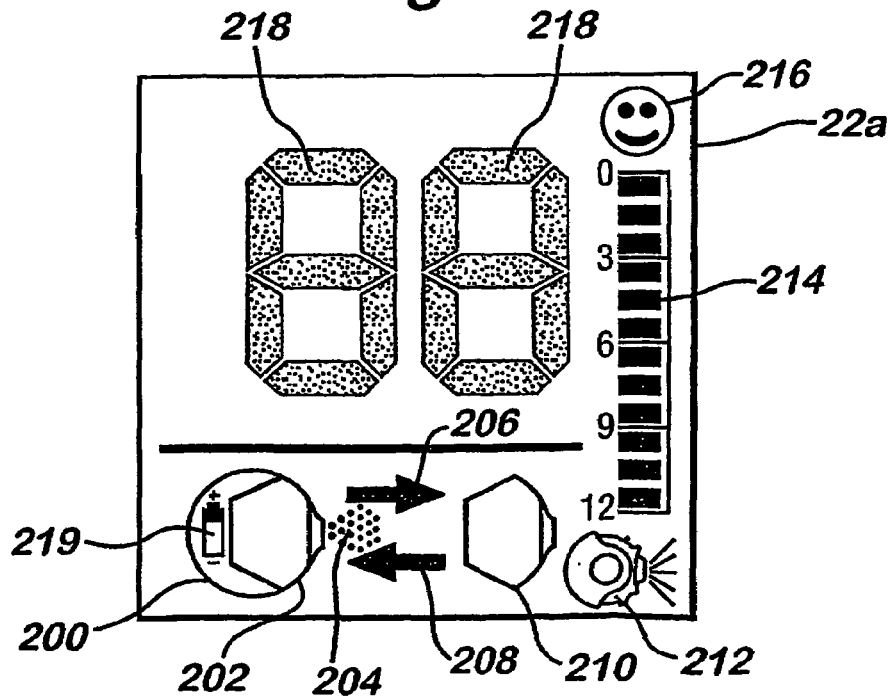
FIGS. 9, 18, 19, 20, 21, and 22 illustrate alternative screen display configurations.

Referring now to FIG. 9, the display screen includes a number of icons and indicia, all of which are separately controllable by the control unit 90. In this screen configuration, the display includes indicia in the form of a base unit icon 200, a refill attached icon 202, a dose primed icon 204, a remove refill icon 206, an attached refill icon 208, a refill unattached icon 210, a dose due icon 212, time elapsed indicia 214, dose not due icon 216, dose count indicia 218 and low battery level icon 219.

As shown in FIG. 9, the base unit icon 200 and the refill attached icon 202 are located adjacent one another, and form a representation of the entire medicament dispenser, providing a simplified outline corresponding to the external appearance of the medicament dispenser as a whole when the cover 10 has been moved to its dispensing position (see for example FIGS. 3*a* and 3*b*). Note that the base unit icon 200 defines a contained area representing an area within the base unit, within which the low battery level icon 219 is placed. This aids understanding of the low battery level condition when generated. Namely, by placing the low battery level icon 219 within the contained area defined by the base unit icon 200, the user can better understand that it is the base unit which requires replacement due to the low battery level condition. The holder 20 is preferably sealed in such a way that the user cannot readily replace the battery within the base unit. Instead, the user is instructed to return the base unit and obtain a new base unit whereby to carry out the remainder of his treatment regimen.

Note further that the display of the refill attached icon 202 is separately controllable from the display of the base unit icon 200. Thus, by hiding the refill attached icon 202, various different sensed conditions may be indicated to the user in a manner in which the understanding of the condition is increased. Such conditions include the refill attached condition, the refill not attached condition, the refill authenticated condition, the refill invalid condition, the low dose remaining condition and the no dose remaining condition, all of which may involve the selected hiding of the refill attached icon, either statically during the indication of the condition, or by alternately activating and hiding the icon to cause the icon to blink, thereby indicating to the user that the condition relates to the refill cassette 30. Furthermore, the refill unattached icon 210 which includes components similar in form to the refill attached icon, may be selectively controlled to display various conditions, in combination with the refill attached icon 202, including the refill attached condition (in which case the refill unattached icon 210 can be hidden in a static display), the refill attached condition, the refill invalid condition, and the no dose remaining condition, in all of which cases the refill unattached icon 210 may be statically displayed or switched on and off alternately.

A further graphical representation of the base unit is used in this embodiment as the dose due icon 212, along with indicia, which form part of the dose due icon 212, indicating the dispensing of medicament therefrom, for example in the form of a plume emanating from the mouthpiece of the dispenser represented by the icon 212.

The time elapsed indicia 214 consist of a plurality of separately activatable elements, which for example each separately indicated a further period elapsed since the time of last taking. The dose count indicia 218 consist of a segmented numerical character display, of which the individual segments are separately controllable to represent a number between 0 and 99.

FIGS. 10 to 17 illustrate use of the display configuration illustrated in FIG. 9 to display various conditions sensed by the medicament dispenser to a user. Note that the display is, under the default operating conditions, not activated, in order to reduce the power consumption of the battery within the base unit. However, when the cover 10 is opened, the cover open sensor 94 senses the opening of the cover, and in response control unit 90 displays the current operating conditions of the medicament dispenser on the display 22. Similarly, when a user presses button 24, as sensed by button switch 98, the control unit may activate display 22 to indicate the current operating conditions of the medicament dispenser. After a preset period of inactivity by the user, the display may again be powered down. Alternatively, the display may be driven continuously, providing sufficient battery power is provided; this can simplify the electronic subsystem of the dispenser.

Figure 10:
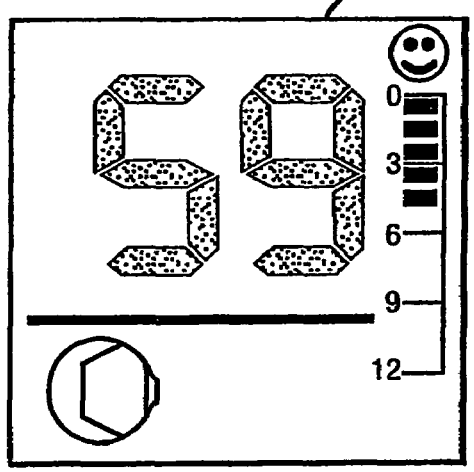
FIGS. 10 to 17 illustrate various display states used to indicate different sensed conditions of the medicament dispenser.

FIG. 10 illustrates the activation of indicia on the display 22*a* under normal operating conditions of the dispenser. In this state, the refill is attached and authenticated, hence refill attached icon 202 is activated in conjunction with the display of the base unit icon 200. All other icons in the lower half of the screen are however hidden. The refill contains 59 doses, hence the dose count indicia 218 are selectively activated to display the numerals "59". Furthermore, the time elapsed since last dose taking is five hours, hence five segments of the time elapsed indicia are activated and the remainder are hidden. Furthermore, since the time elapsed is within the reminder period interval, the dose not due icon 216 is also switched on.

Figure 11:
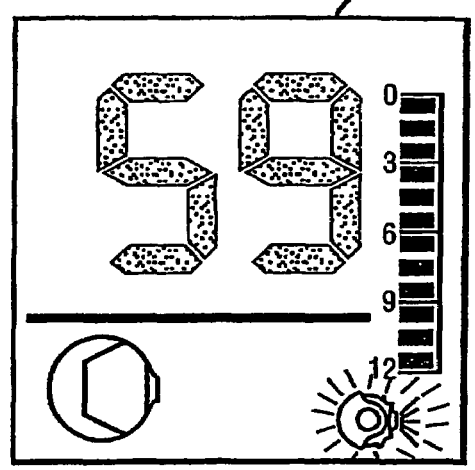

FIG. 11 shows the display 22*a* seven hours after the condition shown in FIG. 10. In this state, the time elapsed indicia are all activated, since the time is 12 hours or over since the last dose, and the dose due icon 212 is activated. Preferably, the dose due icon 212 is alternately switched on and off to highlight to the user that their dose is due.

Figure 12:
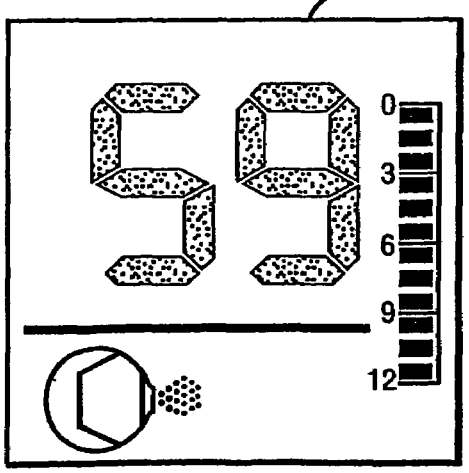

FIG. 12 illustrates the state of the display 22*a* following from the state indicated in FIG. 11, once the user has primed the index leader of the medicament dispenser. Once primed, the dose primed icon 204 is activated to indicate that the user should now inhale from the mouthpiece. The dose primed indicator includes a representation of powder located next to the mouthpiece on the refill attached icon 202.

Figure 13:
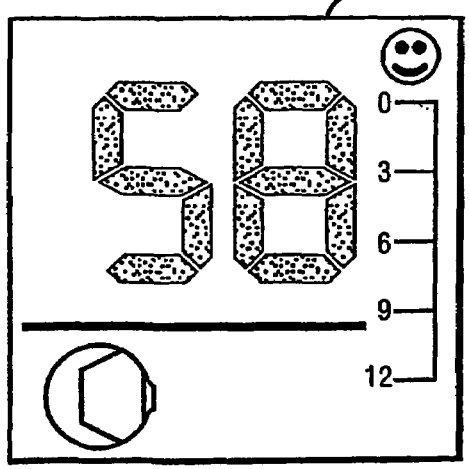

FIG. 13 illustrates the state of the display 22*a* once inhalation of the medicament indicator to be available in the display shown in FIG. 12 is performed by the user. Inhalation of the medicament is detected by inhalation sensor 106, following which the dose primed icon 204 is switched off, or switched between an alternating display state and a static display state. Furthermore, the dose not due icon 216, which was removed once the time elapsed exceeded the reminder interval is activated once more, and the time elapsed indicia are switched off to indicate that it is less than one hour since a dose was last taken. Furthermore, the dose count indicia 218 are controlled to decrement the numerical value shown thereby. Whilst the dose count is reduced here in response to the detection of inhalation of the medicament, the dose count indicia may also be controlled to decrement the numerical value shown in response to the dose primed condition, since in this state the dose has in fact been dispensed, although not yet inhaled, from the refill cassette 30.

A further possible feature, which is not shown in the display 22*a*, is an overexposed dose indicator feature. According to this feature, after the dose primed condition, at which point the dose is first exposed to the atmosphere, a dose exposure period is initiated in the timer of the control unit 90. After a predetermined interval, for example 2 hours, if the user has not yet inhaled the dose, as detected by inhalation sensor 106, a further set of indicia may be displayed on the display 22*a* to indicate that the dose should not be taken by the user, for example by using a cross-shaped icon over the dose primed icon.

Figure 14A:
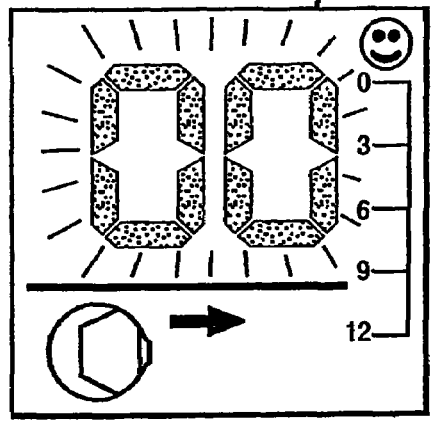
Figure 14B:
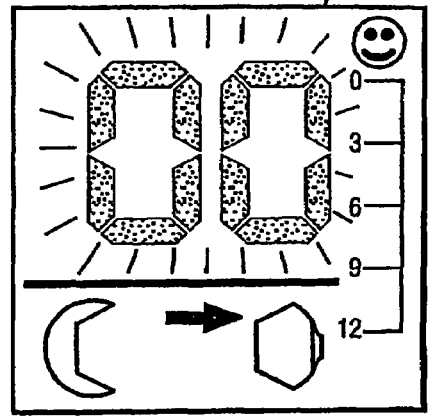

Referring now to FIGS. 14*a* and 14*b*, after all of the doses available in the refill cassette 30 are dispensed, the dose count becomes zero, as shown in FIGS. 14*a* and 14*b*. At this point, the no dose remaining condition is indicated on the display. In this condition, the dose counting indicia may be switched on and off alternately. Furthermore, the display state shown in FIG. 14*a* may be alternated with the display state shown in FIG. 14*b*. Thus, the refill attached icon 202 is alternately switched on and off. The removed refill icon 206 is statically activated, and the refill unattached icon 210 is alternately switched on and off, in counter to the switching on and off of the refill attached icon 202, so that the removal of the refill cassette 30 is indicated in an animated display sequence, along with the use of the arrow-shaped icon also indicating such movement to indicate that the empty refill should be removed.

Figure 15:
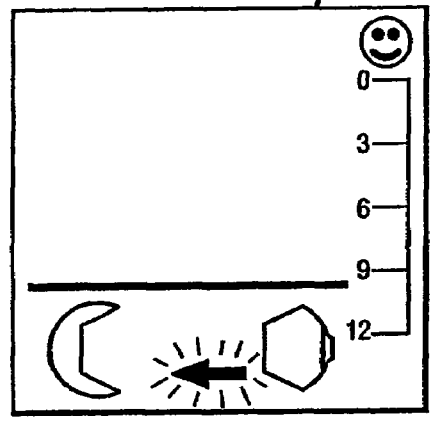

When the empty refill is removed by the user, the refill attached sensor 96 generates a refill unattached condition in the control unit 90, which then controls the display to show a state as shown in FIG. 15. In this state, the dose count indicia are switched off, the refill attached icon 202 is hidden, the refill unattached icon 210 is activated, and the attach refill icon 208, in the form of an arrow located between the refill unattached icon 210 and the base unit icon 200 and pointing towards the base unit 200, is alternately switched on and off to indicate insertion of a new refill cassette 30 into the holder 20.

Figure 16:
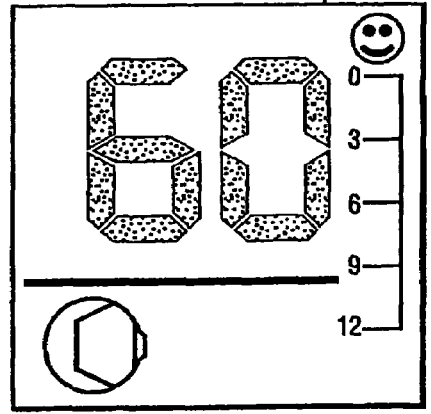

FIG. 16 illustrates the display state used when a fresh refill, containing 60 doses, is attached to the base unit 200. The display is similar to that shown in FIG. 10. Note that the time elapsed indicia in this case are all switched off, since the refill cassette is inserted shortly after the last dose taking by the user. However, in the case that the refill cassette is replaced some time after the last dose taking, sufficient to have one or more of the time elapsed indicia displayed, the control unit 90 maintains the time elapsed period monitor during the refill replacement procedure, such that the time elapsed period continues to be monitored and indicated without interruption during a replacement procedure.

Figure 17A:
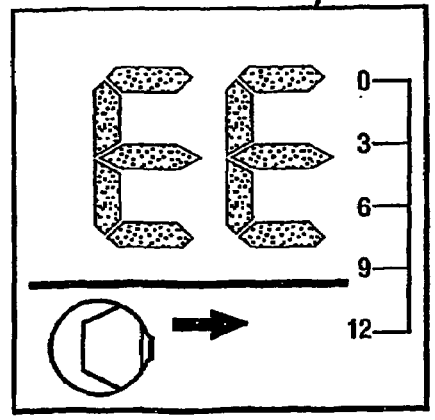
Figure 17B:
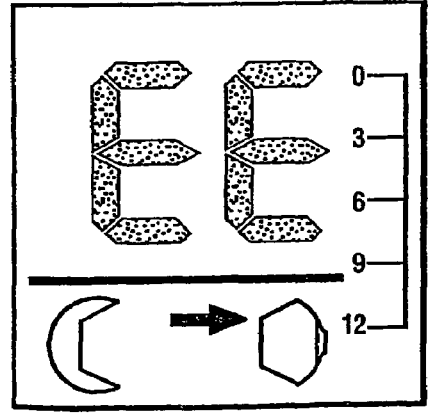

FIGS. 17*a* and 17*b* illustrate the display state used when the refill invalid condition is generated by the control unit 90. In this state, the screens shown in FIG. 17*a* and that shown in FIG. 17*b* are alternately activated. In the state shown in FIG. 17*a*, the dose count indicia are altered to show a non-numerical set of characters (for example EE) and the remove refill sequence, similar to that shown in FIGS. 14*a* and 14*b*, is used to indicate that the refill should be replaced with a genuine refill.

Figure 18:
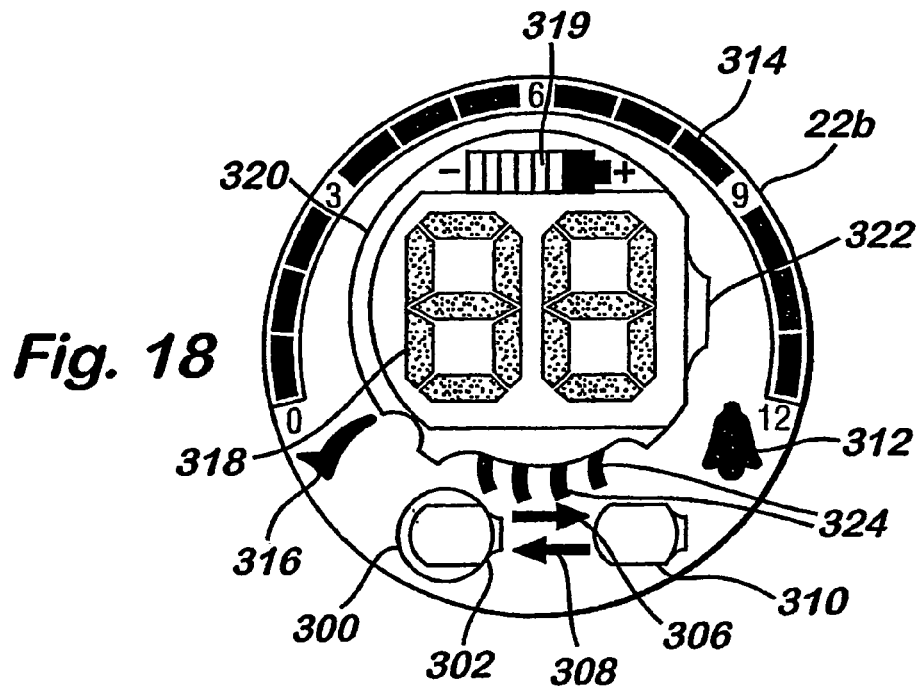

FIG. 18 illustrates a further configuration screen display 22*b*. In this configuration, the base unit icon 300, the refill attached icon 302, the remove refill icon 306, the attach refill icon 308 and the refill unattached icon 310 have similar configurations and functions as corresponding elements of the screen display 22*a*. The dose due icon 312, the time elapsed indicia 314 and the dose not due icon 316 have different configurations but similar functions to that illustrated in FIG. 9. In this case, the dose count indicia 318 are located within a large refill icon 322, which is a graphical representation of the external appearance of at least parts of the refill cassette 30, including its mouthpiece, and within a contained area defined by a large base unit icon 320. Furthermore, the low battery level icon 319 is located within a contained area defined by the large base unit 320. By locating the dose count indicia 318 within the contained area defined by the refill icon 322 and/or the base unit icon 320, the understanding of the feature that the doses are contained within the refill cassette 30 is increased, and the understanding that the battery is located within the base unit is also increased, thereby increasing the user's understanding of the functioning of the device. Furthermore, additional dose due icons 324 are used to indicate that actuation of the indexing lever is required. The icons 324 provide a graphical representation of the thumbtab of the index lever adjacent the base unit icon 320, and may be displayed alternately to indicate movement of the thumbtab of the index lever, thereby to indicate to the user that the index lever should be primed when a dose is due.

Figure 19:
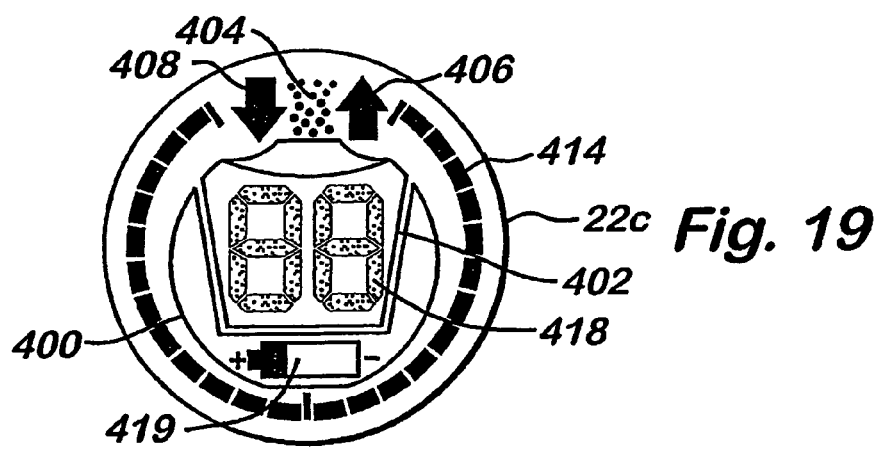

FIG. 19 illustrates a further configuration of a screen display 22*c*. In this screen display, the configurations of each of the base unit icon 400, the refill attached icon 402, the dose primed icon 404, the remove refill icon 406, the attach refill icon 408, the time elapsed indicia 414, the dose count indicia 418 and the low battery level icon 419 have different configurations to that shown in FIG. 9, but the functionality is the same as that described. In this configuration, the dose count indicia 418 are located in a contained area within the refill attached icon 402, and the battery icon 419 is located within the base unit icon 400, to increase conciseness and understandability of the indications given.

Figure 20:
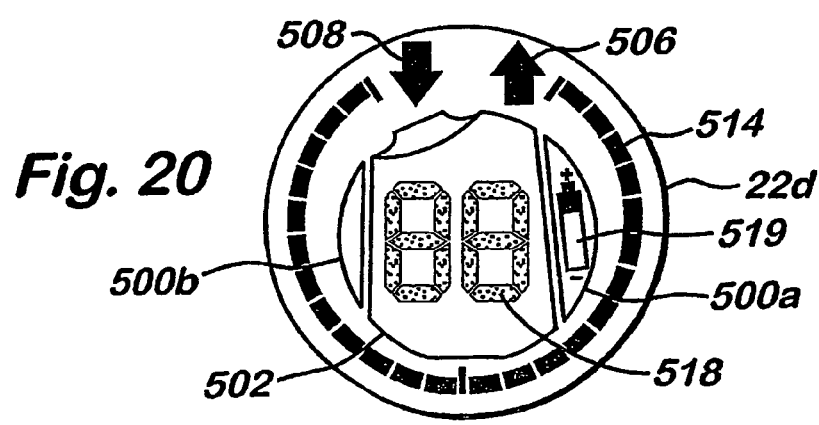

FIG. 20 illustrates an alternative screen display configuration 22*d*, similar to that shown in FIG. 19. However, in this case, the base unit icon 500*a*, 500*b* is split into two separate parts which enclose the refill icon 502. One of the parts, part 500*a*, contains the low battery level icon 519.

Figure 21:
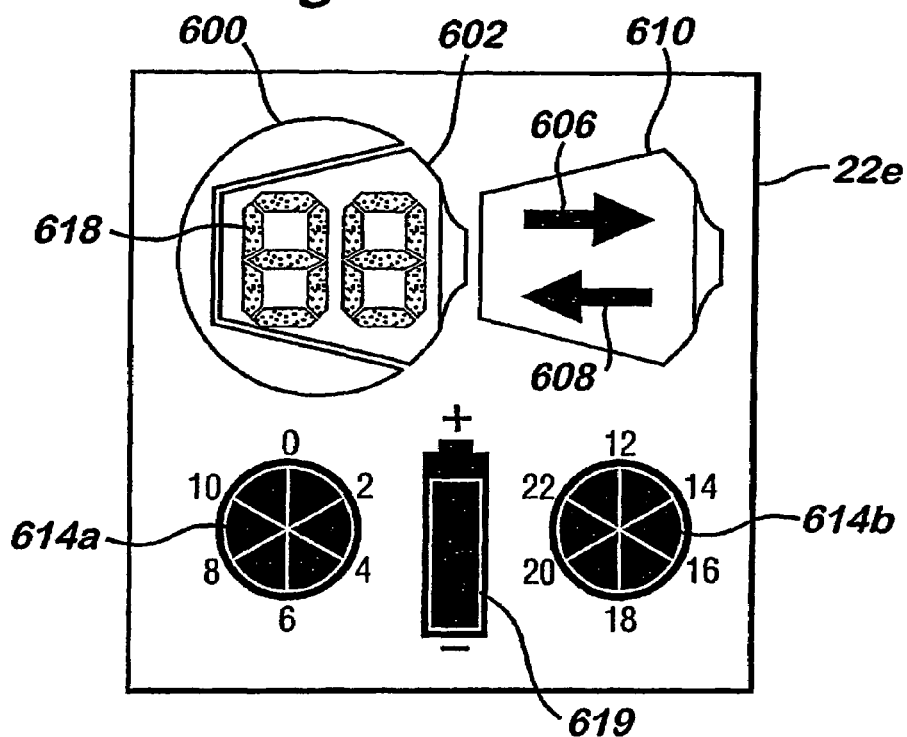

FIG. 21 illustrates a further alternative screen display configuration 22*e*. In this configuration, all of the base unit icon 600, the refill icon 602, the remove refill icon 616, the attach refill icon 608, the refill unattached icon 610, the time elapsed indicia 614a, 614b, the dose count indicia 218 and the low battery level icon 619 are configured differently to that shown in FIG. 9, but the functionality is the same. In this embodiment, the dose count indicia 618 are contained within the refill attached icon 602 and the remove refill icon and the attach refill icon 608 are contained within the refill unattached icon 610, to increase understandability of the display state within a constrained area. Namely, by placing the remove refill icon 606 and the attach refill icon 608 within the refill unattached icon, the refill unattached icon 610 may be increased in size without requiring a larger display. In this embodiment, the time elapsed indicia are divided into two parts 614a, 614b, each containing a circular segmented display each corresponding to sequential 12 hours periods respectively.

Figure 22:
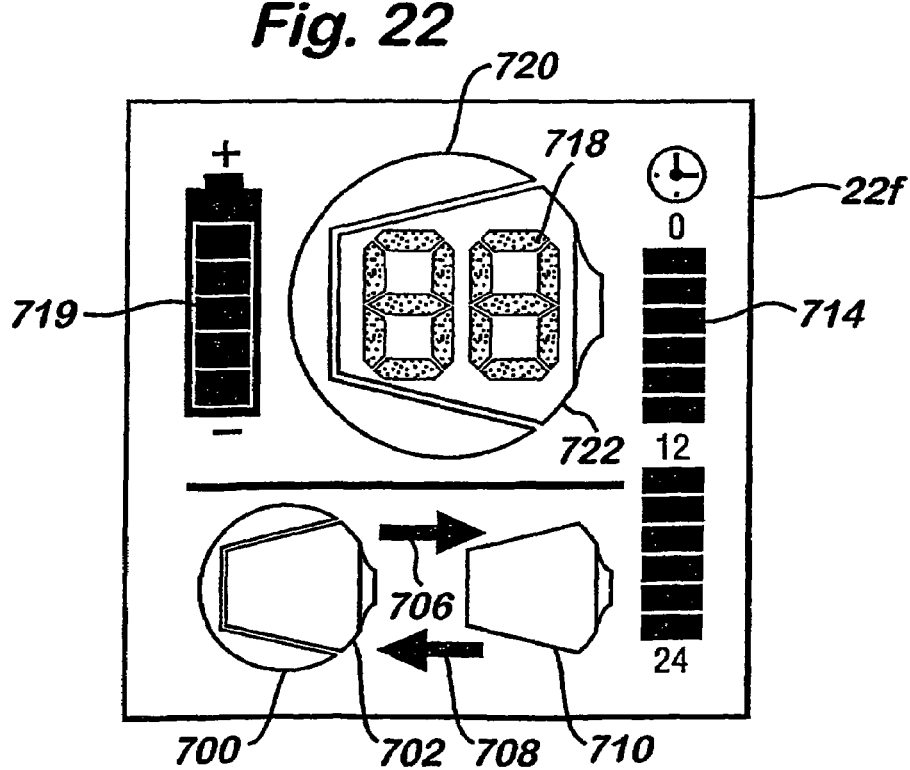

FIG. 22 illustrates a further alternative configuration of display screen 22f. In this configuration, the base unit icon 700, the refill attached icon 702, the remove refill icon 704, the attach refill icon 706, the refill unattached icon 710, the time elapsed indicia 714, the dose count indicia 718, the low battery level icon 719, the large base unit icon 720 and the large refill attached icon 722 have different configurations but have corresponding functions to the similar elements shown in FIG. 18. Note that the large base unit icon and the large refill attached icon 722 may be activated and hidden, i.e. switched on and off, in unison with the smaller base unit icon 700 and refill attached icon 702, to increase understanding of the current condition of the device to the user.

Note that alternative embodiments to those described above are envisaged. As an inhalation device, the dispensing outlet is in the form of a mouthpiece through which a user can inhale to access the medicament in the opened container. However, the medicament dispenser may take forms of other than an inhalation device, for example a capsule dispenser, a liquid dispenser or a syringe.

The cassette 30 described above includes includes a mouthpiece as a dispensing outlet. The dispensing outlet may alternatively have any suitable form ranging from a simple orifice to a shaped passage (e.g. cone or tube) to a mouthpiece or nozzle.

The medicament carrier may carry medicament in a variety of forms including dry powder, granule, aerosol suspension, solution including aqueous solution, capsule, nebule, pellet and tablet carrier form.

The medicament carrier respectively may itself have a variety of forms other than that described including a capsule; a tablet; an aqueous solution; an aerosol; and a reservoir carrying multiple doses of medicament in a dry powder form or a liquid form.

In the above, the display 22 takes the form of a segmented LCD display. The display may take other forms, for example, comprise a screen such as an LED arrangement or a pixellated LCD display. The display may be embodied using analogue or digital technology.

In the above, detectors are used to sense a condition of the medicament detector. Suitably, any actuation detector or release detector comprises a sensor for detecting any suitable parameter such as movement. Any suitable sensors are envisaged including the use of optical sensors and electrical contact switches. The release detector may sense any parameter affected by release of the medicament such as pressure, temperature, sound, moisture, carbon dioxide concentration and oxygen concentration.

In the above, the base unit includes a first transceiver for transmitting and receiving data and in association with the medicament carrier, whilst the refill cassette includes a second transceiver for transmitting and receiving data, wherein data is transferable in two-way fashion from the first transceiver to the second transceiver. The data is preferably in digital form and suitable for transfer by electronic or optical means. A medicament dispenser of this general type is described in pending UK Patent Application No. 0020538.5, the contents of which are included herein by reference.

In one embodiment herein, a history of the usage of the medicament dispenser is transferred to the second transceiver. When the blister strip in the cassette is exhausted it is exchanged by the patient for a new refill cassette. At the point of exchange, which will typically occur at the pharmacy, data may be transferred from the exhausted cassette to the refill and vice-versa. Additionally, usage history data may be read from the refill and transferred to a healthcare data management system for example comprising a network computer system under the control of a healthcare data manager.

In the above embodiments, the medicament carrier is manually indexed. In an alternative embodiment, the base unit includes an electronic motor, preferably an ultrasonic motor, for rotating the index wheel 60 and the lid-winding wheel 70 in response to actuation of a switch, for example by the user pushing a button.

A medicament dispenser according to the invention is suitable for dispensing medicament, particularly for the treatment of respiratory disorders such as asthma and chronic obstructive pulmonary disease (COPD).

Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (e.g. s the sodium salt), ketotifen or nedocromil (e.g. as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or 6α, 9α-difluoro-11β-hydroxy-16α-methyl-3-oxo-17α-propionyloxy-androsta-1,4-diene-17β-carbothioic acid S-(2-oxo-tetrahydrofuran-3-yl) ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; adenosine 2a agonists, e.g. 2R,3R,4S,5R)-2-[6-Amino-2-(1S-hydroxymethyl-2-phenyl-ethylamino)-purin-9-yl]-5-(2ethyl-2H-tetrazol-5-yl)-tetrahydro-furan-3,4-diol (e.g. as maleate); $\alpha_4$ integrin inhibitors e.g. (2S)-3-[4-({[4-(aminocarbonyl)-1-piperidinyl]carbonyl}oxy)phenyl]-2-[((2S)-4-methyl-2-{[2-(2-methylphenoxy) acetyl]amino}pentanoyl) amino] propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred medicaments are selected from albuterol, salmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) or formoterol (e.g. as the fumarate salt) in combination with an antiinflammatory steroid such as a beclomethasone ester (e.g., the dipropionate) or a fluticasone ester (e.g., the propionate) or budesonide. A particularly preferred combination is a combination of fluticasone propionate and salmeterol, or a salt thereof particularly the xinafoate salt). A further combination of particular interest is budesonide and formoterol (e.g. as the fimarate salt).

Generally, powdered medicament particles suitable for delivery to the bronchial or alveolar region of the lung have an aerodynamic diameter of less than 10 micrometers, preferably less than 6 micrometers. Other sized particles may be used if delivery to other portions of the respiratory tract is desired, such as the nasal cavity, mouth or throat. The medicament may be delivered as pure drug, but more appropriately, it is preferred that medicaments are delivered together with excipients (carriers) which are suitable for inhalation. Suitable excipients include organic excipients such as polysaccharides (i.e. starch, cellulose and the like), lactose, glucose, mannitol, amino acids, and maltodextrins, and inorganic excipients such as calcium carbonate or sodium chloride. Lactose is a preferred excipient.

Particles of the powdered medicament and/or excipient may be produced by conventional techniques, for example by micronisation, milling or sieving. Additionally, medicament and/or excipient powders may be engineered with particular densities, size ranges, or characteristics. Particles may comprise active agents, surfactants, wall forming materials, or other components considered desirable by those of ordinary skill.

The excipient may be included with the medicament via well known methods, such as by admixing, co-precipitating and the like. Blends of excipients and drugs are typically formulated to allow the precise metering and dispersion of the blend into doses. A standard blend, for example, contains 13000 micrograms lactose mixed with 50 micrograms drug, yielding an excipient to drug ratio of 260:1. Dosage blends with excipient to drug ratios of from 100:1 to 1:1 may be used. At very low ratios of excipient to drug, however, the drug dose reproducibility may become more variable.

It will be understood that the present disclosure is for the purpose of illustration only and the invention extends to modifications, variations and improvements thereto, and that any elements of the different embodiments may be combined to form further embodiments of the invention.

Note that, in other applications of the invention, the base unit, refill container and/or medicament carrier may take a variety of different forms. Correspondingly, the icons or other graphical representations used may similarly take a variety of different forms. The invention may be used for purposes other than informing a taker of medicament; for example the display functionality may be used for training purposes and for informing and/or warning caregivers.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the appended claims.

The invention claimed is:

1. A medicament dispenser comprising a base unit, the base unit being adapted for receiving a replaceable refill container and for sensing one or more conditions of the medicament dispenser, said base unit comprising display means for displaying indicia representing a state of the medicament dispenser, wherein:

said display means are configured to display first indicia providing a graphical representation of the base unit; and said display means are configured to display second indicia providing a graphical representation of a refill container, wherein the dispenser is adapted such that the display of at least one of said first and said second indicia is selectively controllable independently of the display of the other of said first and said second indicia in order to indicate said one or more sensed conditions of the medicament dispenser.

2. A medicament dispenser according to claim 1, wherein the base unit is adapted for sensing one or more conditions of the refill container.

3. A medicament dispenser according to claim 1, wherein said second indicia are selectively controllable independently of the display of said first indicia.

4. A medicament dispenser according to claim 1, wherein the base unit is adapted for sensing one or more conditions of the base unit.

5. A medicament dispenser according to claim 1, wherein said first indicia are selectively controllable independently of the display of said second indicia.

6. A medicament dispenser according to claim 1, wherein said first and said second indicia are displayable together in a graphical representation of the base unit with a refill container attached thereto.

7. A medicament dispenser according to claim 1, wherein said base unit includes a mechanical priming component for initiating the dispensing of medicament and wherein said display means is configured to display indicia providing a graphical representation of actuation of the mechanical priming component, the display of the mechanical priming indicia being selectively controllable in accordance with a sensed condition of the mechanical priming component.

8. A medicament dispenser comprising a base unit, the base unit being adapted for receiving a replaceable refill container and for sensing one or more conditions of the medicament dispenser, said base unit comprising display means for displaying indicia representing a state of the medicament dispenser, wherein:

said display means are configured to display first indicia providing a graphical representation of the base unit; and said display means are configured to display second indicia providing a graphical representation of a refill container, wherein the dispenser is adapted such that the display of at least one of said first and said second indicia is selectively controllable independently of the display of the other of said first and said second indicia in order to indicate said one or more sensed conditions of the medicament dispenser, wherein said base unit includes a mechanical priming component for initiating the dispensing of medicament and wherein said display means is configured to display indicia providing a graphical representation of actuation of the mechanical priming component, the display of the mechanical priming indicia being selectively controllable in accordance with a sensed condition of the mechanical priming component, and wherein the dispenser is arranged to monitor medicament reminder periods, the display of the mechanical priming indicia being selectively controllable in accordance with a timing condition relating to a medicament reminder period.

9. A medicament dispenser comprising a base unit, the base unit being adapted for receiving a replaceable refill container and for sensing one or more conditions of the medicament dispenser, said base unit comprising display means for displaying indicia representing a state of the medicament dispenser, wherein:

said display means are configured to display first indicia providing a graphical representation of the base unit; and said display means are configured to display second indicia providing a graphical representation of a refill container, wherein the dispenser is adapted such that the display of at least one of said first and said second indicia is selectively controllable indecendently of the display of the other of said first and said second indicia in order to indicate said one or more sensed conditions of the medicament dispenser wherein said one or more sensed conditions comprise a medicament quantity condition.

10. A medicament dispenser according to claim 9, wherein said display means are further configured to display indicia representing a medicament remaining in the form of numeric characters.

11. A medicament dispenser according to claim 10, wherein said refill container contains a plurality of discrete medicaments and said numeric characters represent the number of discrete medicaments remaining.

12. A medicament dispenser according to claim 10, wherein the second indicia define a contained area representing an area inside the refill container and said medicament quantity indicia are located in said contained area.

13. A medicament dispenser according to claim 9, wherein said one or more sensed conditions comprise a no medicament remaining condition, or a low medicament remaining condition.

14. A medicament dispenser according to claim 13, wherein said dispenser is configured, in response to said one or more sensed conditions, to alternately display and hide said first and/or said second indicia.

15. A medicament dispenser comprising a base unit, the base unit being adapted for receiving a replaceable refill container and for sensing one or more conditions of the medicament dispenser, said base unit comprising display means for displaying indicia representing a state of the medicament dispenser, wherein:

said display means are configured to display first indicia providing a graphical representation of the base unit; and said display means are configured to display second indicia providing a graphical representation of a refill container, wherein the dispenser is adapted such that the display of at least one of said first and said second indicia is selectively controllable indenendentlv of the display of the other of said first and said second indicia in order to indicate said one or more sensed conditions of the medicament dispenser wherein said display means is configured to display further indicia representing removal of the refill container from the base unit.

16. A medicament dispenser according to claim 15, wherein said removal indicia comprise indicia in the form of an arrow shape.

17. A medicament dispenser according to claim 15, wherein said removal indicia comprise indicia providing a graphical representation of at least part of the external appearance of a refill container.

18. A medicament dispenser comprising a base unit, the base unit being adapted for receiving a replaceable refill container and for sensing one or more conditions of the medicament dispenser, said base unit comprising display means for displaying indicia representing a state of the medicament dispenser, wherein:

said display means are configured to display first indicia providing a graphical representation of the base unit; and said display means are configured to display second indicia providing a graphical representation of a refill container, wherein the dispenser is adapted such that the display of at least one of said first and said second indicia is selectively controllable independently of the display of the other of said first and said second indicia in order to indicate said one or more sensed conditions of the medicament dispenser wherein said display means are configured to display further indicia representing attachment of a refill container to the base unit.

19. A medicament dispenser according to claim 18, wherein said attachment indicia comprise indicia in the form of an arrow shape.

20. A medicament dispenser according to claim 18, wherein said attachment indicia comprise indicia providing a graphical representation of at least part of the external appearance of a refill container.

21. A medicament dispenser according to claim 1, wherein said one or more sensed conditions comprise a condition at to whether or not a refill container is attached.

22. A medicament dispenser comprising a base unit, the base unit being adapted for receiving a replaceable refill container and for sensing one or more conditions of the medicament dispenser, said base unit comprising display means for displaying indicia representing a state of the medicament dispenser, wherein:

said display means are configured to display first indicia providing a graphical representation of the base unit; and said display means are configured to display second indicia providing a graphical representation of a refill container, wherein the dispenser is adapted such that the display of at least one of said first and said second indicia is selectively controllable independently of the display of the other of said first and said second indicia in order to indicate said one or more sensed conditions of the medicament dispenser, and wherein said one or more sensed conditions comprise a condition as to whether or not which the refill container is validated by the base unit as an authentic refill container.

23. A medicament dispenser according to claim 1, wherein the medicament dispenser is an inhalation device.

24. A medicament dispenser according to claim 20, wherein said dispenser includes a mouthpiece and a sensor for sensing the inhalation of medicament through said mouthpiece.

25. A medicament dispenser according to claim 24, wherein said display means are configured to display indicia representing medicament to be dispensed, and wherein the display of said indicia representing medicament is selectively controllable in accordance with an output of said inhalation sensor.

26. A medicament dispenser according to claim 1, wherein said one or more sensed conditions comprise a condition in which medication has been dispensed to an output part of the dispenser.

27. A medicament dispenser comprising a base unit, the base unit being adapted for receiving a replaceable refill container, said base unit comprising a display for displaying indicia representing a state of the medicament dispenser, wherein said display means are configured to display:
   first indicia providing a graphical representation of a physical appearance of at least part of the medicament dispenser; and
   second indicia representing one or more sensed conditions of the medicament dispenser,
   wherein said medicament dispenser includes a mechanical priming component for initiating the dispensing of medicament and said second indicia comprise indicia representing actuation of the mechanical priming component.

28. A medicament dispenser comprising a base unit, the base unit being adapted for receiving a replaceable refill container, said base unit comprising a display for displaying indicia representing a state of the medicament dispenser, wherein said display means are configured to display:
   first indicia providing a graphical representation of a physical appearance of at least part of the medicament dispenser; and
   second indicia representing one or more sensed conditions of the medicament dispenser,
   wherein said medicament dispenser includes a mechanical priming component for initiating the dispensing of medicament and said second indicia comprise indicia representing actuation of the mechanical priming component, and
   wherein the dispenser is arranged to monitor medicament reminder periods, the display of the mechanical priming indicia being selectively controllable in accordance with a timing condition relating to a medicament reminder period.

29. A medicament dispenser comprising a base unit, the base unit being adapted for receiving a replaceable refill container and for sensing one or more conditions of the medicament dispenser, said base unit comprising display means for displaying indicia representing a state of the medicament dispenser, wherein:
   said display means are configured to display first indicia providing a graphical representation of the base unit; and
   said display means are configured to display second indicia providing a graphical representation of a refill container,
   wherein the dispenser is adapted such that the display of at least one of said first and said second indicia is selectively controllable independently of the display of the other of said first and said second indicia in order to indicate said one or more sensed conditions of the medicament dispenser, and
   wherein said base unit comprises:
   a cover; and
   a holder, shaped to fit within said body and movable relative to the cover,
   wherein said refill container is receivable by said holder, and wherein movement of the holder relative to the cover results in movement of the refill container between a first position and a second position such that the refill container is reversibly removable from the holder when the refill container is in the second position.

30. A medicament dispenser according to claim 29, wherein medicament is dispensable from said dispenser when the tefill container is in the first position.

31. A medicament dispenser according to claim 30, wherein the medicament dispenser is arranged to actuate said display means in response to movement of said refill container from said second position to said first position.

32. A medicament dispenser according to claim 1, wherein the medicament is in a form selected from the group consisting of capsule; a tablet; an aqueous solution; an aerosol; and a dry powder.

33. A medicarnent dispenser comprising a base unit, the base unit being adapted for receiving a replaceable refill container and for sensing one or more conditions of the medicament dispenser, said base unit comprising display means for displaying indicia representing a state of the medicament dispenser, wherein:
   said display means are configured to display first indicia providing a graphical representation of the base unit; and
   said display means are configured to display second indicia providing a graphical representation of a refill container,
   wherein the dispenser is adapted such that the display of at least one of said first and said second indicia is selectively controllable independently of the display of the other of said first and said second indicia in order to indicate said one or more sensed conditions of the medicament dispenser, and
   wherein the refill container comprises a medicament carrier comprising an elongate strip formed from a base sheet having a plurality of recesses spaced along its length and a lid sheet peelably sealed in superposed relationship thereto to define a plurality of blisters, each for containing medicament therein.

34. A medicament dispenser comprising a base unit, the base unit being adapted for receiving a replaceable refill container and for sensing one or more conditions of the medicament dispenser, said base unit comprising display means for displaving indicia representing a state of the medicament dispenser, wherein said display means are configured to display:
   said display means are configured to display first indicia providing a graphical representation of the base unit; and
   said display means are configured to display second indicia providing a graphical representation of a refill container,
   wherein the dispenser is adapted such that the display of at least one of said first and said second indicia is selectively controllable independently of the display of the other of said first and said second indicia in order to indicate said one or more sensed conditions of the medicament dispenser, and wherein the base unit comprises a first transceiver for receiving data from a second transceiver located on the refill container.

35. A medicament dispenser according to claim 1, wherein the medicament is selected from the group consisting of albuterol, salmeterol, fluticasone propionate and beclomethasone dipropionate and salts or solvates thereof and any combination thereof.

36. A method of dispensing medicament comprising the steps of
(i) providing of a medicament dispenser according to claim 1 and
(ii) dispensing medicament therefrom.

* * * * *